US012667247B2

(12) United States Patent
Kabumoto et al.

(10) Patent No.: US 12,667,247 B2
(45) Date of Patent: Jun. 30, 2026

(54) MEDICAL INSTRUMENT, NASAL ADAPTER, AND BITE BLOCK

(71) Applicant: NIHON KOHDEN CORPORATION, Tokyo (JP)

(72) Inventors: Kenichiro Kabumoto, Tokorozawa (JP); Fumihiko Takatori, Tokorozawa (JP); Masayuki Inoue, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 362 days.

(21) Appl. No.: 18/254,990

(22) PCT Filed: Nov. 24, 2021

(86) PCT No.: PCT/JP2021/043022
§ 371 (c)(1),
(2) Date: May 30, 2023

(87) PCT Pub. No.: WO2022/118716
PCT Pub. Date: Jun. 9, 2022

(65) Prior Publication Data
US 2024/0023790 A1 Jan. 25, 2024

(30) Foreign Application Priority Data
Dec. 2, 2020 (JP) ................................. 2020-200259

(51) Int. Cl.
*A61M 16/06* (2006.01)
*A61B 1/00* (2006.01)
*A61M 16/08* (2006.01)

(52) U.S. Cl.
CPC ..... *A61B 1/00154* (2013.01); *A61M 16/0683* (2013.01); *A61M 16/085* (2014.02)

(58) Field of Classification Search
CPC ............ A61M 16/0672; A61M 16/085; A61M 16/0683; A61M 16/0666; A61M 16/0493;
(Continued)

(56) References Cited

U.S. PATENT DOCUMENTS 9,687,623 B2 6/2017 Colman et al.
2006/0042631 A1 3/2006 Martin et al.
(Continued)

FOREIGN PATENT DOCUMENTS

EP 2 523 719 A1 11/2012
EP 3 546 006 A2 10/2019
(Continued)

OTHER PUBLICATIONS

Office action issued in Japanese Patent Application No. 2020-200259, dated May 7, 2024.
(Continued)

*Primary Examiner* — Victoria Hicks Fisher
(74) *Attorney, Agent, or Firm* — McDonald Hopkins LLC

(57) ABSTRACT

A medical instrument is adapted to be attached to a subject. A nasal adapter includes cannulas adapted to be disposed so as to face nostrils of the subject when the medical instrument is attached to the subject. A bite block includes a hollow member-adapted to be disposed in an oral cavity of the subject when the medical instrument is attached to the subject. A flexible joint connects the nasal adapter and the bite block.

8 Claims, 12 Drawing Sheets

(58) Field of Classification Search
CPC ............ A61M 16/0488; A61M 16/049; A61M
16/0497; A61M 16/0677; A61M 16/0688;
A61M 16/0694; A61M 15/08; A61M
15/085; A61M 2210/0618; A61B
1/00154; A61B 5/682; A61B 5/6819
See application file for complete search history.

(56) References Cited

U.S. PATENT DOCUMENTS

| | | |
|---|---|---|
| 2006/0042632 A1 | 3/2006 | Bishop et al. |
| 2006/0042633 A1 | 3/2006 | Bishop et al. |
| 2006/0042634 A1 | 3/2006 | Nalagatla et al. |
| 2006/0042635 A1 | 3/2006 | Niklewski et al. |
| 2006/0042636 A1 | 3/2006 | Nalagatla et al. |
| 2006/0042637 A1 | 3/2006 | Martin et al. |
| 2006/0042638 A1 | 3/2006 | Niklewski et al. |
| 2006/0081257 A1 | 4/2006 | Krogh et al. |
| 2006/0081258 A1 | 4/2006 | Nalagatla et al. |
| 2006/0081259 A1 | 4/2006 | Bruggeman et al. |
| 2006/0106345 A1 | 5/2006 | Flaker et al. |
| 2006/0278238 A1 | 12/2006 | Borody |
| 2009/0133699 A1 | 5/2009 | Nalagatla et al. |
| 2010/0262033 A1 | 10/2010 | Colman et al. |
| 2011/0245579 A1 | 10/2011 | Bruggeman et al. |
| 2012/0330111 A1 | 12/2012 | Borody |
| 2013/0338522 A1 | 12/2013 | Colman et al. |
| 2016/0228035 A1 | 8/2016 | Poormand et al. |
| 2019/0298956 A1 | 10/2019 | Takatori et al. |
| 2020/0268999 A1* | 8/2020 | Chang ............... A61M 16/0683 |

FOREIGN PATENT DOCUMENTS

| | | |
|---|---|---|
| JP | 2008-511399 A | 4/2008 |
| JP | 2019-170455 A | 10/2019 |
| WO | 2011-085427 A1 | 7/2011 |
| WO | 2019-173869 A1 | 9/2019 |

OTHER PUBLICATIONS

International Search Report dated Feb. 23, 2022 issued in PCT/JP2021/043022.
Written Opinion dated Feb. 23, 2022 issued in PCT/JP2021/043022.
Japanese Office Action issued in Japanese Patent Application No. 2025-038986 dated Aug. 26, 2025.

* cited by examiner

[Fig. 1]
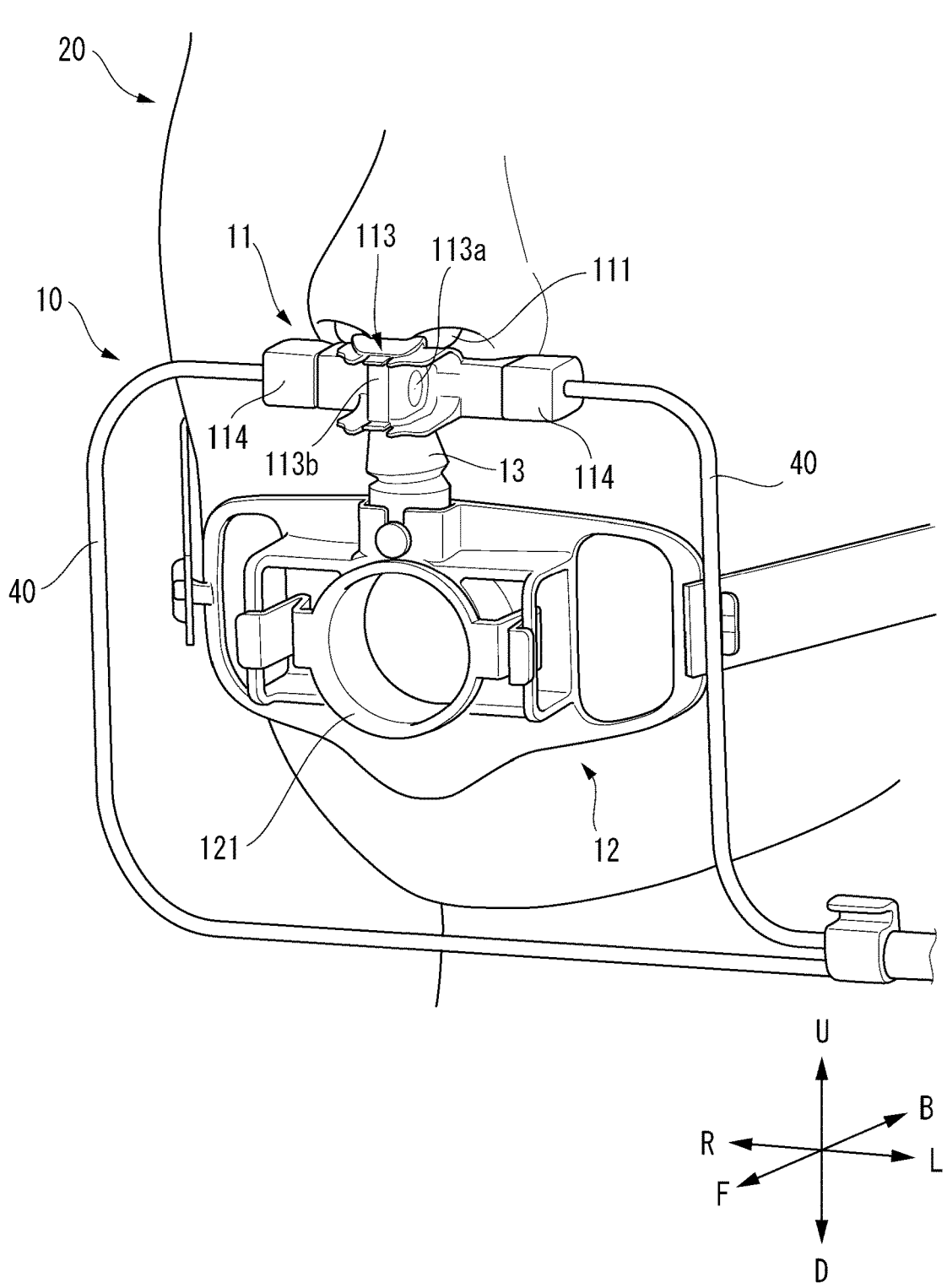

[Fig. 2]
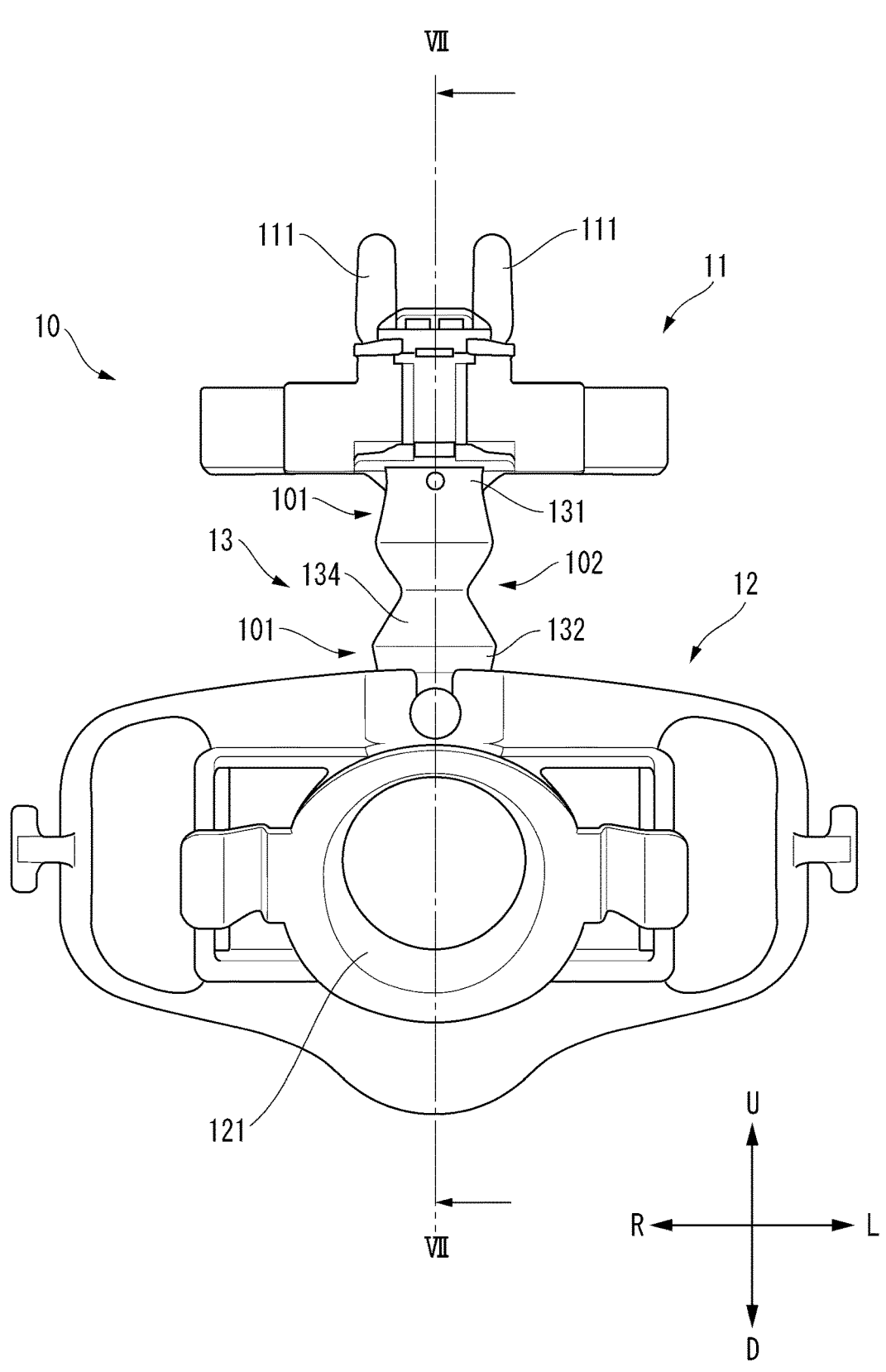

[Fig. 3]
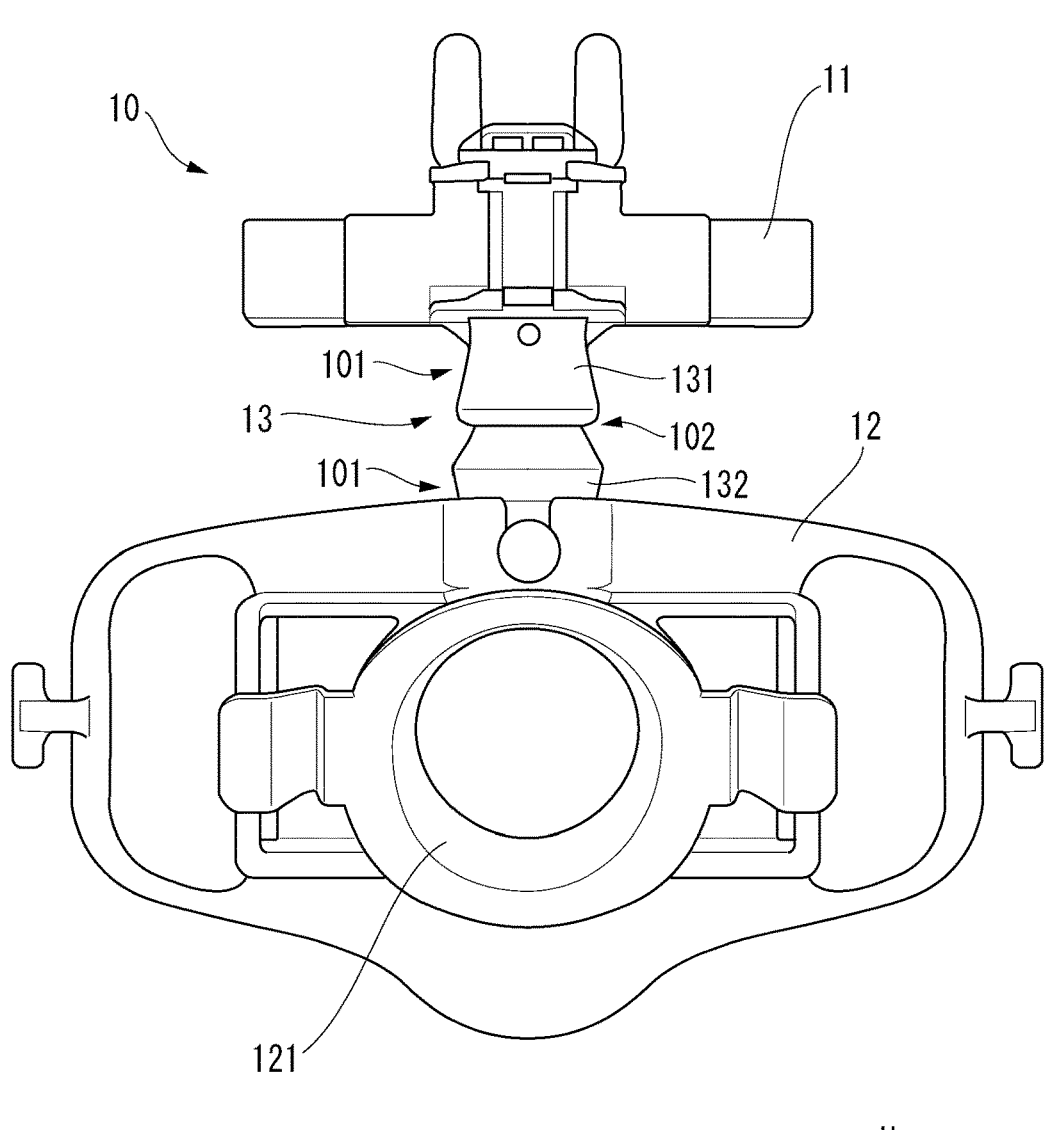
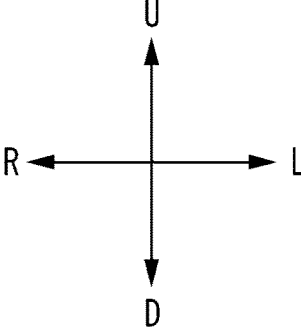

[Fig. 4]
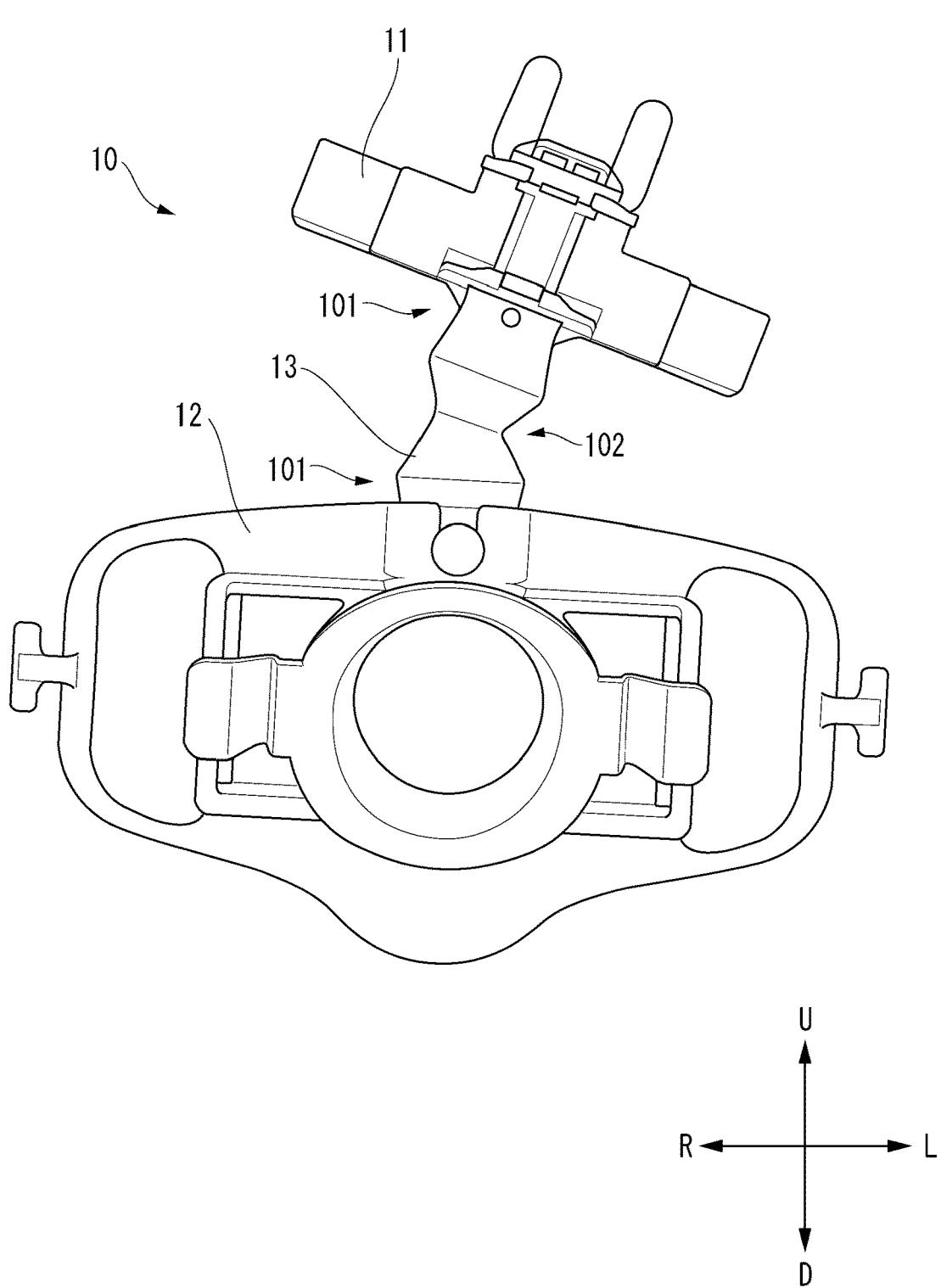

[Fig. 5]
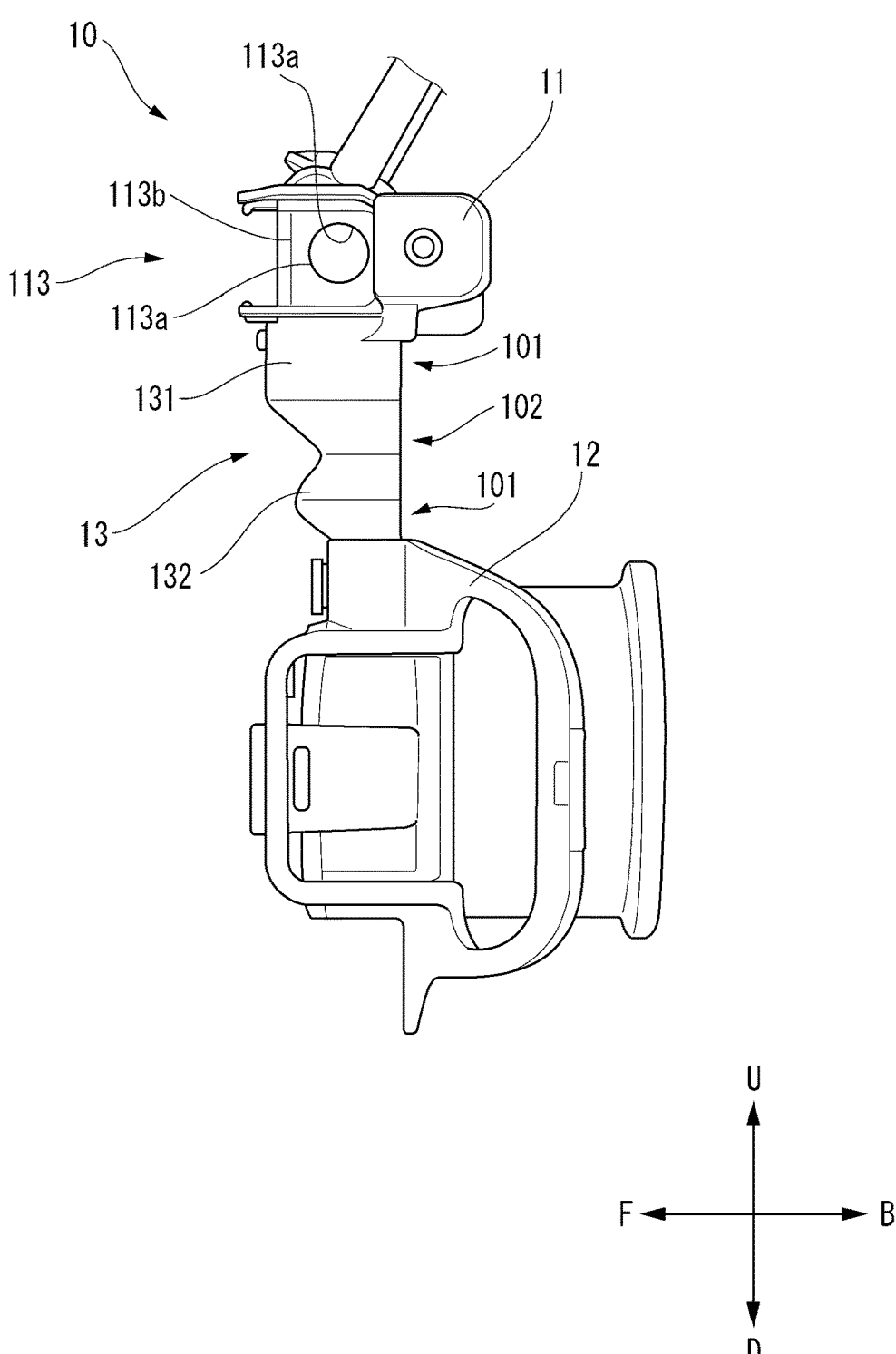

[Fig. 6]
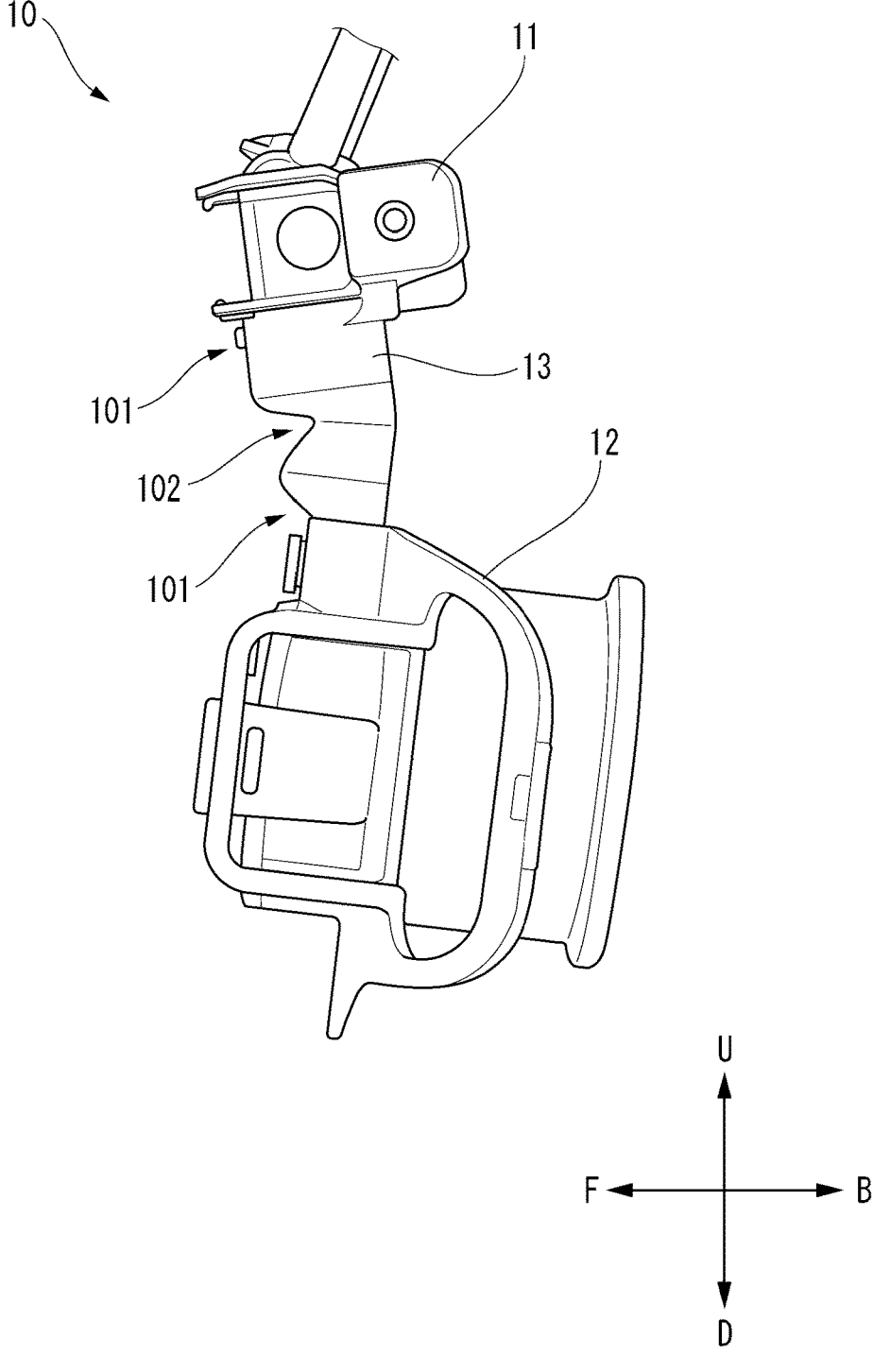

[Fig. 7]
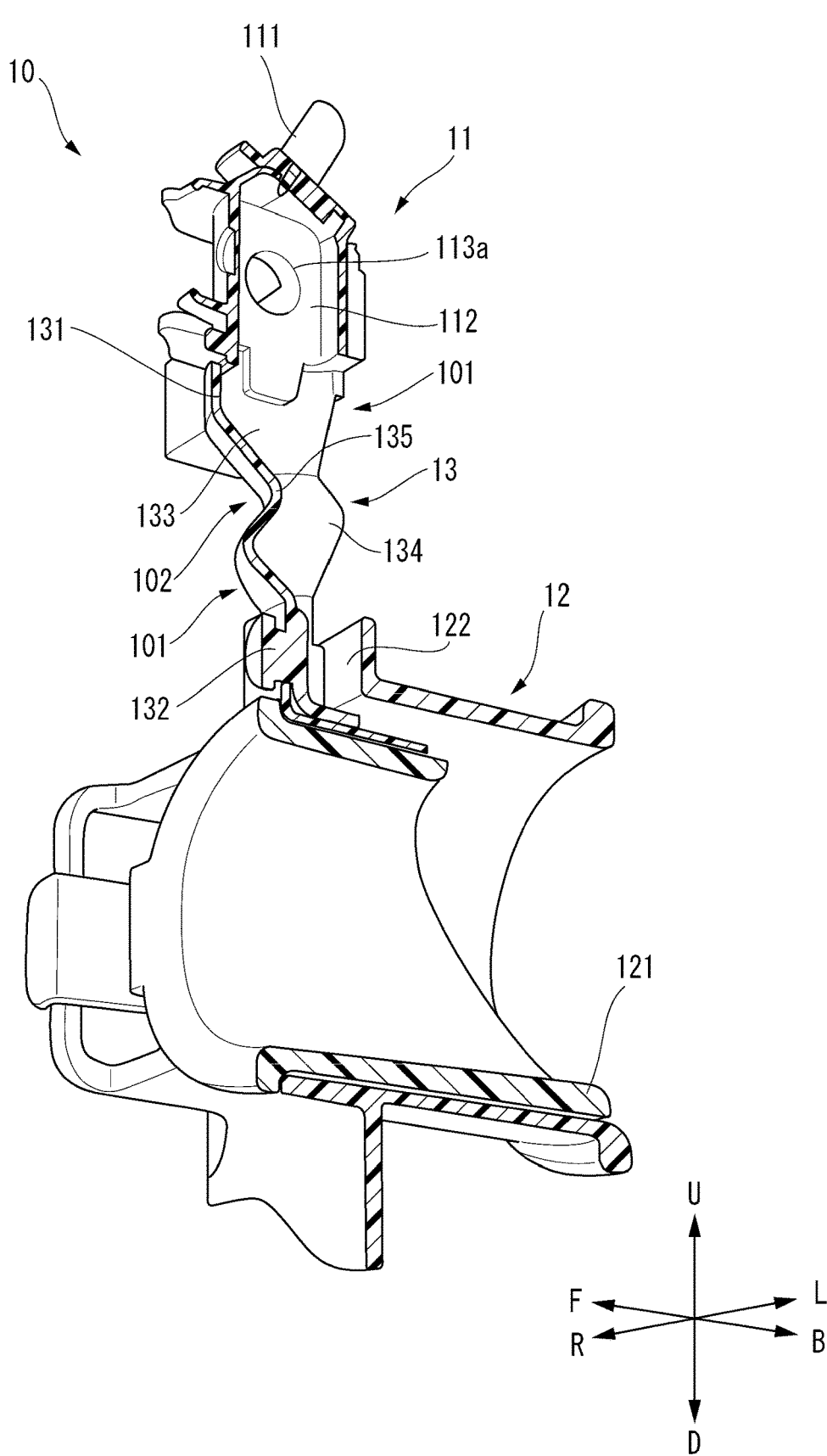

[Fig. 8]
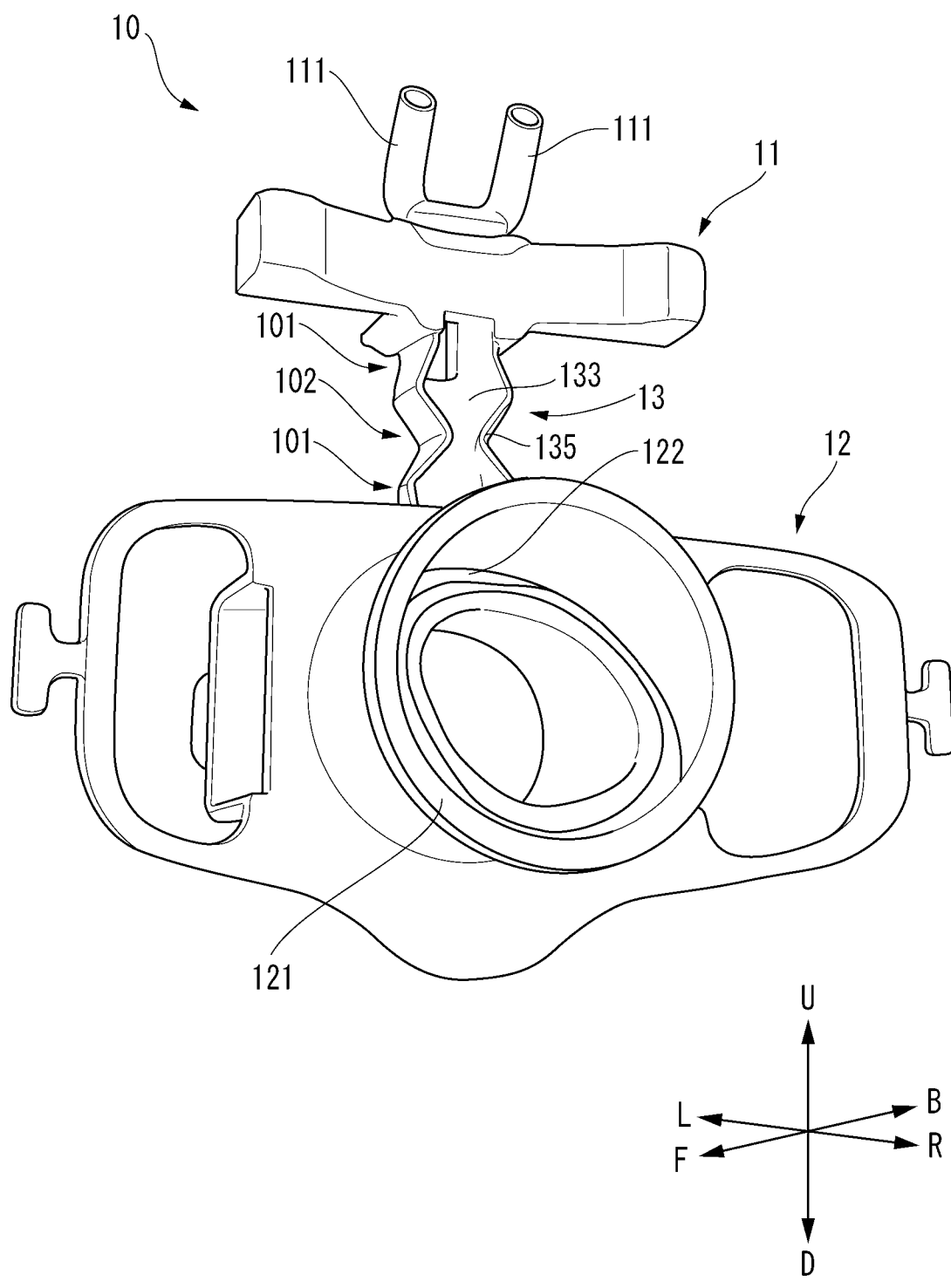

[Fig. 9]
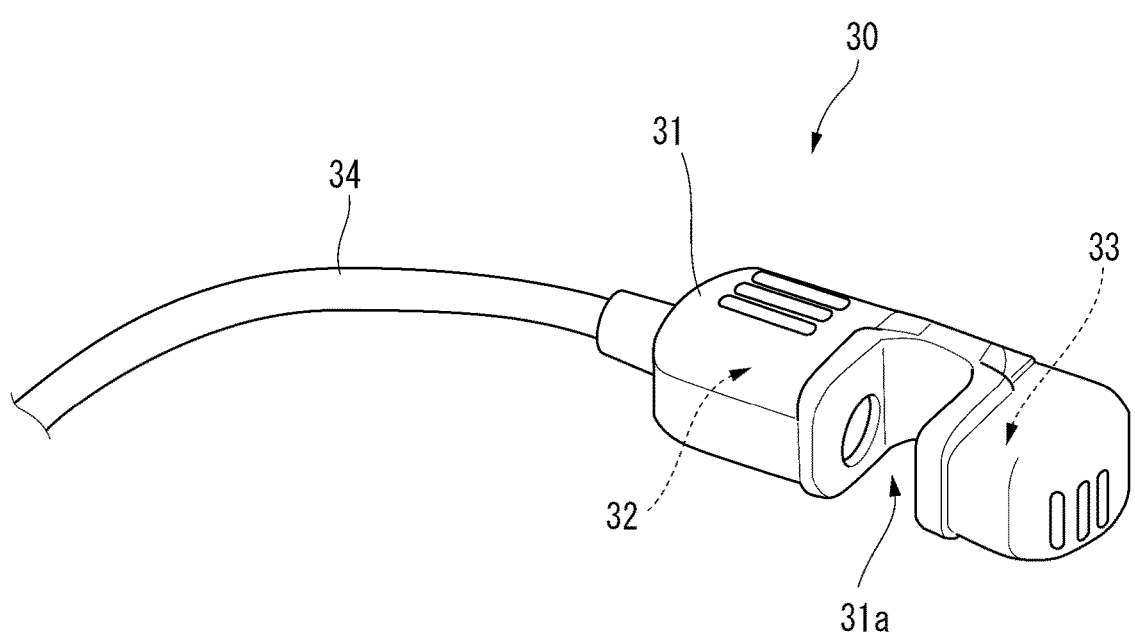

[Fig. 10]
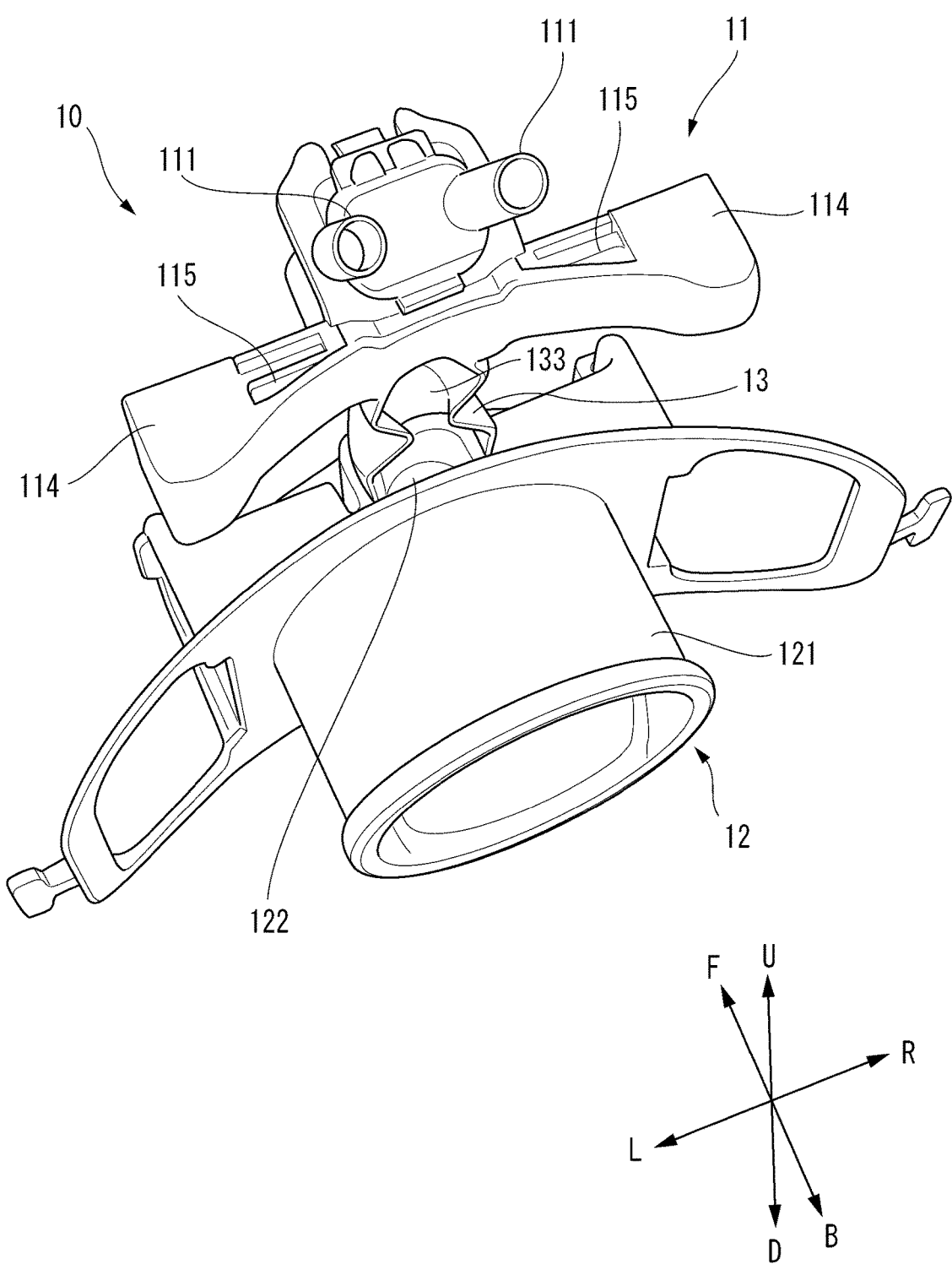

[Fig. 11]
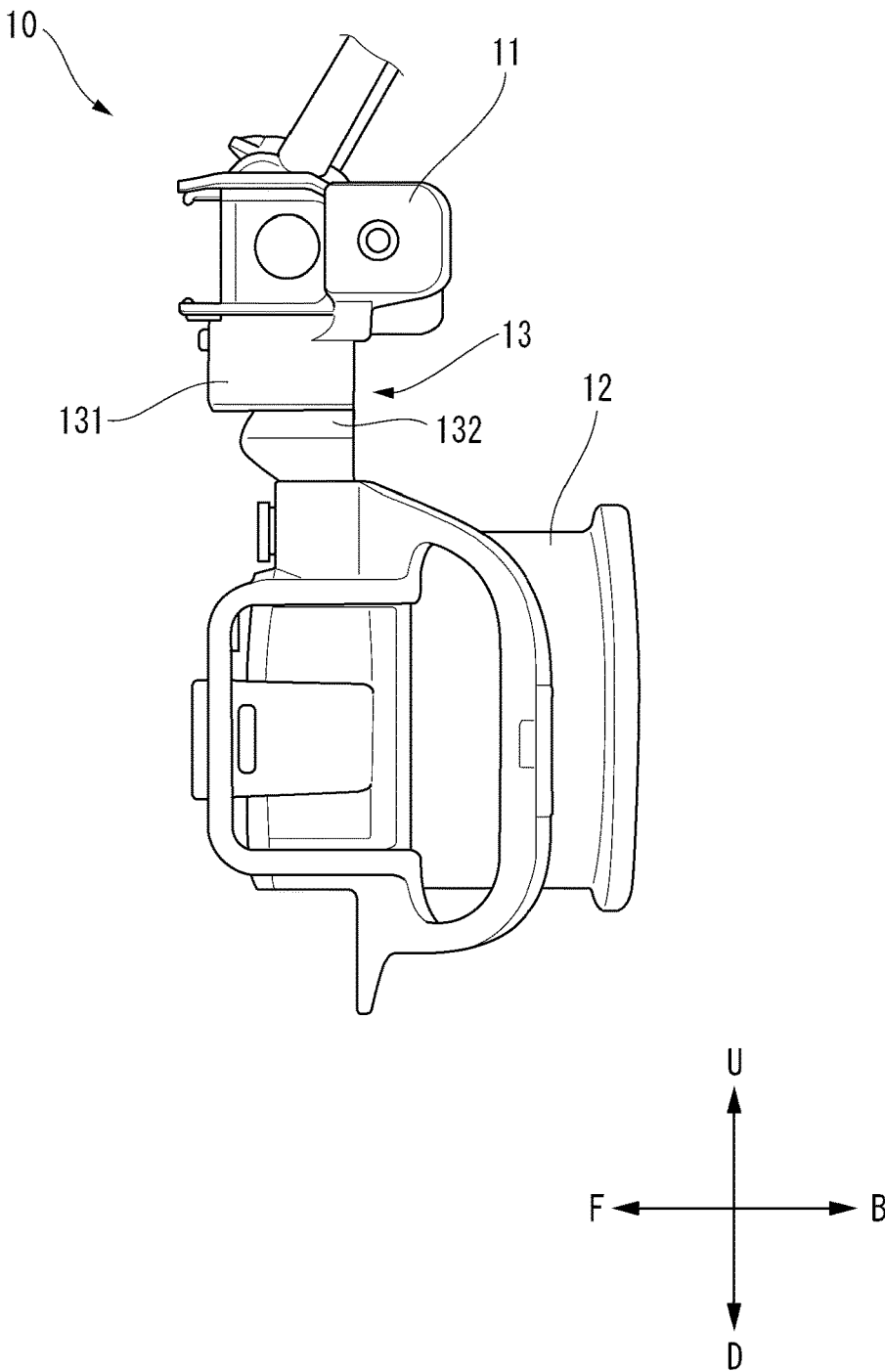

[Fig. 12]
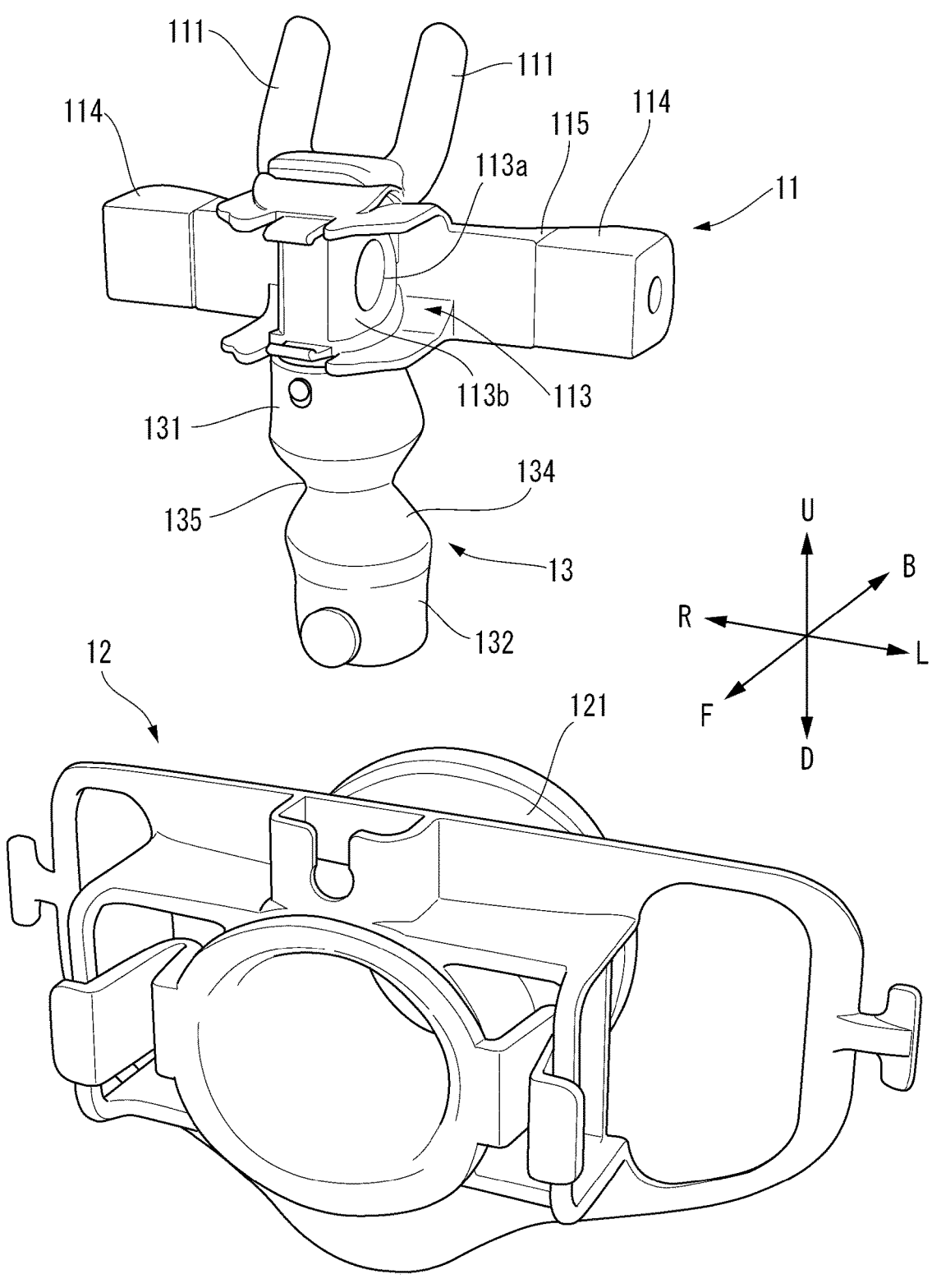

MEDICAL INSTRUMENT, NASAL ADAPTER, AND BITE BLOCK

TECHNICAL FIELD

The presently disclosed subject matter relates to a medical instrument adapted to be attached to a subject for medical purposes. The medical instrument includes a nasal adapter and a bite block. The nasal adapter is provided with an airway section that is adapted to be disposed so as to face nostrils of the subject when the medical instrument is attached to the subject. The bite block is provided with a hollow member that is adapted to be disposed in an oral cavity of the subject when the medical instrument is attached to the subject.

BACKGROUND

U.S. Pat. No. 9,687,623 discloses a medical instrument including a nasal adapter and a bite block as described above. The instrument is used to assist in the acquisition of physiological information of a subject with a respiratory sensor and an endoscope. The nasal adapter has cannulas. When the instrument is attached to the subject, the cannulas are inserted into the nostrils of the subject. The exhaled air that is led out from the nostrils through the cannulas is subjected to detection by the respiration sensor. The endoscope is inserted through the hollow member to be protected from teeth or the like of the subject. The nasal adapter and the bite block are connected by a joint. As a result, changes in the relative positions between them during the acquisition of the physiological information are suppressed.

SUMMARY

Technical Problem

It is demanded to enhance the convenience of the medical instrument including the nasal adapter and the bite block.

Solution to Problem

In order to meet the above demand, an illustrative aspect of the presently disclosed subject matter provides a medical instrument adapted to be attached to a subject, comprising:

a nasal adapter including an airway section adapted to be disposed so as to face nostrils of the subject when the medical instrument is attached to the subject;

a bite block including a hollow member adapted to be disposed in an oral cavity of the subject when the medical instrument is attached to the subject; and a joint having flexibility and connecting the nasal adapter and the bite block.

In order to meet the above demand, an illustrative aspect of the presently disclosed subject matter provides a nasal adapter adapted to be attached to a subject, comprising:

an airway section adapted to be disposed so as to face nostrils of the subject when the nasal adapter is attached to the subject; and a joint having flexibility and configured to connect a bite block provided with a hollow member adapted to be disposed in an oral cavity of the subject to the nasal adapter.

In order to meet the above demand, an illustrative aspect of the presently disclosed subject matter provides a bite block adapted to be attached to a subject, comprising:

a hollow member adapted to be disposed in an oral cavity of the subject when the bite block is attached to the subject; and a joint having flexibility and configured to connect a nasal adapter provided with an airway section adapted to be disposed so as to face nostrils of the subject to the bite block.

According to body movements of the subject, operations of a medical instrument that is inserted into the oral cavity of the subject through the hollow member, or the like, there is a case where an external force that changes the relative positions of the nasal adapter and the bite block is applied to the medical instrument that has been attached to the subject.

According to the configuration of each of the illustrative aspects, the relative positions of the nasal adapter and the bite block are actively changed due to the flexibility of the joint, so that the external force can be absorbed or dissipated. As a result, it is possible to suppress positional deviation of the airway section of the nasal adapter caused by the external force. Therefore, the convenience of the medical instrument including the nasal adapter and the bite block can be enhanced.

BRIEF DESCRIPTION OF DRAWINGS

FIG. 1 illustrates a state where a medical instrument according to one embodiment is attached to a subject.

FIG. 2 illustrates an appearance of the medical instrument of FIG. 1 as viewed from a front side.

FIG. 3 illustrates an exemplary state where a joint of the medical instrument of FIG. 1 is deformed.

FIG. 4 illustrates another exemplary state where the joint of the medical instrument of FIG. 1 is deformed.

FIG. 5 illustrates an appearance of the medical instrument of FIG. 1 as viewed from a left side.

FIG. 6 illustrates another exemplary state where the joint of the medical instrument of FIG. 1 is deformed.

FIG. 7 illustrates a cross section along the line VII-VII in FIG. 2 as viewed from an arrowed direction.

FIG. 8 illustrates an appearance of the medical instrument of FIG. 1 as viewed from a rear side.

FIG. 9 illustrates an optical sensor adapted to be attached to the medical instrument of FIG. 1.

FIG. 10 illustrates an appearance of the medical instrument of FIG. 1 as viewed from a top side.

FIG. 11 illustrates another exemplary state where the joint of the medical instrument of FIG. 1 is deformed.

FIG. 12 illustrates a state where a nasal adapter and a bite block of FIG. 1 are separated.

DESCRIPTION OF EMBODIMENTS

Examples of embodiments will be described in detail below with reference to the accompanying drawings. In the accompanying drawings, an arrow F represents a forward direction of an illustrated structure. An arrow B represents a rearward direction of an illustrated structure. An arrow U represents an upward direction of an illustrated structure. An arrow D represents a downward direction of an illustrated structure. An arrow L represents a left direction of an illustrated structure. An arrow R represents a right direction of an illustrated structure.

FIG. 1 illustrates a state where a medical instrument 10 according to an embodiment is attached to a subject 20. FIG. 2 illustrates an appearance of the medical instrument 10 as viewed from a front side.

The "left" and "right" that are used in the following descriptions indicate a left direction and a right direction as viewed from the subject 20. In a state where the medical instrument 10 is attached to the subject 20, the left-right direction of the medical instrument corresponds to the left-right direction of a head of the subject 20. Similarly, an up-down direction and a front-rear direction of the medical instrument 10 correspond to an up-down direction and a front-rear direction of the head of the subject 20, respectively.

The medical instrument 10 includes a nasal adapter 11, a bite block 12, and a joint 13.

The nasal adapter 11 includes a pair of cannulas 111. Each cannula 111 has a hollow cylindrical shape. The cannulas 111 are inserted into nostrils of the subject 20 when the medical instrument 10 is attached to the subject 20, and are disposed so as to face inner walls of the nostrils. Each cannula 111 is an example of an airway section.

The bite block 12 includes a hollow member 121. The hollow member 121 is disposed so as to be located in an oral cavity of the subject 20 when the medical instrument 10 is attached to the subject 20. The hollow portion of the hollow member 121 is configured to allow a medical instrument such as an endoscope to be inserted therethrough. The hollow member 121 protects the medical instrument from teeth or the like of the subject 20.

The joint 13 connects the nasal adapter 11 and the bite block 12 to each other. Specifically, the joint 13 has a first connecting portion 131 and a second connecting portion 132. The first connecting portion 131 is located at an upper end portion of the joint 13 to be connected to the nasal adapter 11. The second connecting portion 132 is located at a lower end portion of the joint 13 to be connected to the bite block 12.

The joint 13 is formed of, for example, a soft polyvinyl chloride resin, a thermoplastic elastomer, silicone, or the like. The joint 13 has flexibility.

As illustrated in FIGS. 2 to 4, due to the flexibility of the joint 13, the relative positions of the nasal adapter 11 and the bite block 12 can be changed not only in the up-down direction of the medical instrument 10, but also in a plane including the up-down direction and the left-right direction of the medical instrument 10.

Additionally or alternatively, as illustrated in FIGS. 5 and 6, due to the flexibility of the joint 13, the relative positions of the nasal adapter 11 and the bite block 12 may be changed even in a plane including the up-down direction and the front-rear direction of the medical instrument 10. Although not illustrated, due to the flexibility of the joint 13, the relative positions of the nasal adapter 11 and the bite block 12 may change even in a plane including the left-right direction and the front-rear direction of the medical instrument 10.

According to body movements of the subject 20, operations of a medical instrument that is inserted into the oral cavity of the subject 20 through the hollow member 121, or the like, there is a case where an external force that changes the relative positions of the nasal adapter 11 and the bite block 12 is applied to the medical instrument 10 that has been attached to the subject 20. According to the configuration of the present embodiment, the relative positions of the nasal adapter 11 and the bite block 12 are actively changed due to the flexibility of the joint 13, so that the external force can be absorbed or dissipated. As a result, it is possible to suppress positional deviation of the cannulas 111 of the nasal adapter 11 caused by the external force.

Therefore, the convenience of the medical instrument 10 including the nasal adapter 11 and the bite block 12 can be enhanced.

FIG. 7 illustrates a cross section of the medical instrument 10 along the lines VII-VII in FIG. 2 as viewed from the direction of the arrows. FIG. 8 illustrates an appearance of the medical instrument 10 as viewed from a facial side of a subject 20.

The nasal adapter 11 includes a housing defining a first airway 112. The first airway 112 communicates with each cannula 111. The housing is molded with a resin such as polyethylene, polypropylene, or polyethylene terephthalate. These materials are selected as materials that are relatively harder than the joint 13.

The bite block 12 includes a housing defining a second airway 122. The second airway 122 communicates with the hollow member 121. The housing is molded with a resin such as polyethylene, polypropylene, or polyethylene terephthalate. These materials are selected as materials that are relatively harder than the joint 13.

The joint 13 forms a third airway 133. The third airway 133 communicates the first airway 112 and the second airway 122 with each other. Namely, the nostrils and the oral cavity of the subject 20 may be communicated with each other through the first airway 112, the second airway 122, and the third airway 133.

According to the above configuration, the joint 13 that allows changes in the relative positions of the nasal adapter 11 and the bite block 12 after the attachment of the medical instrument 10 to the subject 20 can be used as an airway for communicating the nostrils and the oral cavity of the subject 20. An example of the utilization of the airway configured as described above will be described.

As illustrated in FIGS. 1 and 5, the nasal adapter 11 includes a sensor support 113. The sensor support 113 includes a convex portion 113b formed with a pair of windows 113a. As is apparent from FIGS. 5 and 7, the windows 113a are arranged so as to face each other across the first airway 112.

An optical sensor 30 illustrated in FIG. 9 may be attached to the sensor support 113. The optical sensor 30 includes a housing 31. The housing 31 has a concave portion 31a. The housing 31 accommodates a light emitting element 32 and a light detecting element 33. The light emitting element 32 and the light detecting element 33 are disposed so as to face each other across the concave portion 31a.

The optical sensor 30 includes a lead wire 34. The lead wire 34 includes a signal line that transmits a driving signal from a measurement device (not illustrated) to the light emitting element 32. The light emitted from the light emitting element 32 based on the driving signal passes through the concave portion 31a, and is incident on the light detecting element 33. The light detecting element 33 outputs a detection signal corresponding to the intensity of the incident light. The lead wire 34 also includes a signal line that transmits the detection signal to the measurement device.

When the optical sensor 30 is attached to the sensor support 113, the convex portion 113b is fitted into the concave portion 31a. As a result, the optical sensor 30 is supported by the sensor support 113. At this time, the light emitted from the light emitting element 32 enters the first airway 112 through one of the pair of windows 113a provided in the convex portion 113b. The light that has passed through the first airway 112 is incident on the light detecting element 33 through the other one of the pair of windows 113a.

The optical sensor 30 is used to determine a concentration of a specific gas component contained in an exhaled air of the subject 20. The wavelength of the light emitted from the light emitting element 32 is determined as a wavelength at which the light is significantly absorbed by the specific gas component. Examples of specific gas components include carbon dioxide, anesthetic gas, and the like.

The exhaled air from the nostrils of the subject 20 is guided to the first airway 112 through the cannulas 111. Since the second airway 122 of the bite block 12 communicates with the first airway 112 through the third airway 133 of the joint 13, exhaled air from the oral cavity of the subject 20 into which the hollow member 121 is inserted may also be guided to the first airway 112.

In accordance with the respiration of the subject 20, the concentration of the specific gas component in the first airway 112 located between the light emitting element 32 and the light detecting element 33 of the optical sensor 30 is changed, whereby the intensity of the light detected by the light detecting element 33 is changed. As a result, it is possible to measure a temporal change of the concentration of the gas component in the respiratory air of the subject 20.

As illustrated in FIG. 1, in the present embodiment, the nasal adapter 11 includes a tube connecting portion 114. A gas supply tube 40 is connected to the tube connecting portion 114. The gas supply tube 40 is used for supplying a gas from a gas supply source (not illustrated) to the subject 20. Examples of the gas include oxygen and anesthetic gas.

As illustrated in FIG. 10, the nasal adapter 11 is provided with a pair of gas supply holes 115. Each of the gas supply holes 115 communicates with the gas supply tube 40 connected to the tube connecting portion 114. The gas supply holes 115 are disposed so as to face the nostrils of the subject 20 when the medical instrument 10 is attached to the subject 20. Each of the gas supply holes 115 is an example of the airway section.

The gas that is supplied through the gas supply tube 40 is introduced into the nostrils of the subject 20 through the gas supply holes 115, and may also be introduced into the oral cavity of the subject 20 through the first airway 112 of the nasal adapter 11, the third airway 133 of the joint 13, and the second airway 122 of the bite block 12.

The nasal adapter 11 according to the present embodiment includes both the sensor support 113 and the gas supply holes 115. However, the nasal adapter 11 may be configured to include only one of the sensor support 113 and the gas supply holes 115.

As illustrated in FIGS. 2-8, the medical instrument 10 may include first portions 101 and a second portion 102. The first portions 101 include portions of the third airway 133. The second portion 102 includes another portion of the third airway 133. The second portion 102 has higher flexibility than the first portions 101.

Specifically, as illustrated in FIG. 7, the first portions 101 include a portion corresponding to the first connecting portion 131 and a portion corresponding to the second connecting portion 132 of the joint 13 in the third airway 133. The second portion 102 corresponds to an intermediate portion 134 which is located between the first connecting portion 131 and the second connecting portion 132 in the third airway 133. In this example, the first connecting portion 131, the second connecting portion 132, and the intermediate portion 134 are formed of the same material. However, the first connecting portion 131 and the second connecting portion 132 are respectively supported by the mated nasal adapter 11 and the mated bite block 12 so as to have relatively higher rigidity than the intermediate portion 134. As a result, the second portion 102 has higher flexibility than the first portion 101.

According to the above configuration, even in a case where the relative positions of the nasal adapter 11 and the bite block 12 is actively changed by the deformation of the second portion 102 as illustrated in FIGS. 3, 4, and 6, the deformation of the first portion 101 having relatively higher rigidity is suppressed, whereby occlusion of the third airway 133 due to the deformation of the joint 13 can be hardly occurred. Accordingly, it is possible to maintain the function of the airway communicating the nostrils and the oral cavity of the subject 20 while suppressing the positional deviation of the cannulas 111 and the gas supply holes 115 caused by an external force that is applied after the medical instrument 10 is attached to the subject 20. Particularly in the configuration where the optical sensor 30 is supported by the nasal adapter 11, it is possible to suppress the affection of the positional deviation of the cannulas 111 and/or the occlusion of the third airway 133 to the measurement performed by the optical sensor 30.

As illustrated in FIG. 5, the first connecting portion 131 has a larger dimension than the second connecting portion 132 in the front-rear direction of the medical instrument 10.

According to the above configuration, in a case where the relative positions of the nasal adapter 11 and the bite block 12 are changed in the up-down direction of the medical instrument 10 as illustrated in FIGS. 3 and 11, the intermediate portion 134 can be deformed such that a part of the second connecting portion 132 is accommodated in a part of the first connecting portion 131. As a result, the degree of freedom of displacement of the nasal adapter 11 and the bite block 12 in the up-down direction of the medical instrument 10 can be enhanced.

In order to obtain the above effect, it is possible to employ a configuration wherein the second connecting portion 132 has a larger dimension than the first connecting portion 131 in the front-rear direction of the medical instrument 10. Additionally or alternatively, it is possible to employ a configuration wherein one of the first connecting portion 131 and the second connecting portion 132 has a larger dimension in the left-right direction of the medical instrument 10 than the other.

However, in a case where the optical sensor 30 is supported or the gas supply tube 40 is connected in the nasal adapter 11 like the present embodiment, it is preferable to maintain the shape of a portion of the third airway 133 that is located closer to these elements. Accordingly, it is preferable that the first connecting portion 131 has a larger dimension than the second connecting portion 132 in at least one of the front-rear direction and the left-right direction of the medical instrument 10.

As illustrated in FIGS. 7 and 8, the joint 13 includes a narrowed portion 135. The narrowed portion 135 is a portion where the width of the third airway 133 is narrowed in the front-rear direction and the left-right direction of the medical instrument 10.

According to the above configuration, since it is possible to promote air flow generation in the third airway 133. As a result, the gas fluidity between the nasal adapter 11 and the bite block 12 can be enhanced.

It should be noted that the narrowed portion 135 may be configured such that the width of the third airway 133 in either the front-rear direction or the left-right direction of the medical instrument 10 is narrowed.

In the present embodiment, the narrowed portion 135 is formed in the intermediate portion 134 of the joint 13 corresponding to the second portion 102 of the medical instrument 10. In this case, it is possible to cause the configuration capable of promoting the air flow generation to contribute to promoting the deformation of the joint 13.

In the present embodiment, the narrowed portion 135 has a bellows shape including a plurality of bent portions. Specifically, the narrowed portion 135 exhibits the bellows shape in both the left-right direction and the front-rear direction of the medical instrument 10. In this case, not only the deformation of the joint 13 in the left-right direction and the front-rear direction of the medical instrument 10 as illustrated in FIGS. 4 and 6 can be promoted, but also the deformation of the joint 13 in the up-down direction of the medical instrument 10 as illustrated in FIGS. 3 and 11 can be promoted.

As illustrated in FIG. 12, the nasal adapter 11 and the byte block 12 may be separable. In this example, the joint 13 is detachable from the bite block 12.

According to the above configuration, only one of the nasal adapter 11 and the byte block 12 can be replaced as required.

The joint 13 may be detachable from the nasal adapter 11, or may be detachable from both the nasal adapter 11 and the bite block 12.

The above embodiment is merely exemplary to facilitate understanding of the presently disclosed subject matter. The configuration according to the above embodiment can be appropriately modified or improved without departing from the gist of the presently disclosed subject matter.

In the above embodiment, the intermediate portion 134 of the joint 13 corresponds to the second portion 102 of the medical instrument 10 having higher flexibility. According to the above configuration, by connecting the first connecting portion 131 located in the upper end portion of the joint 13 to the nasal adapter 11, and connecting the second connecting portion 132 located in the lower end portion of the joint 13 to the bite block 12, the relatively higher flexibility can be imparted to the intermediate portion 134 without requiring a specialized configuration.

However, the position of the second portion 102 is not particularly limited as described above as long as a plurality of portions having different flexibilities are provided in the joint 13 in order to avoid the occlusion of the third airway 133.

In addition, a plurality of portions having different flexibilities may be provided by molding the joint 13 with a plurality of materials having different rigidities. Alternatively, a plurality of portions having different flexibilities may be provided by changing the thickness of the joint 13 formed of the same material.

In the above embodiment, the cannulas 111 adapted to be inserted into the nostrils are provided in the nasal adapter 11 in order to direct the exhaled air from the nostrils of the subject 20 to the first airway 112. However, a cup-shaped member defining a space facing the nostrils may be used to direct the exhaled air from the nostrils to the first airway 112. Alternatively, the space may be used for guiding the gas supplied from the gas supply holes 115 to the nostrils. The space is also an example of the airway section.

The phrase "at least one of A and B" as used herein with respect to the two entities A and B is meant to include cases where only A is identified; only B is identified; and both A and B are identified. Each of the entities A and B may be singular or plural unless otherwise noted.

The present application is based on Japanese Patent Application No. 2020-200259 filed on Dec. 2, 2020, the entire contents of which are hereby incorporated by reference.

The invention claimed is:

1. A medical instrument adapted to be attached to a subject, comprising:
    a nasal adapter including:
        a pair of cannulas adapted to be disposed so as to face nostrils of the subject when the medical instrument is attached to the subject, and
        a first housing defining a first airway communicating with the cannulas;
    a bite block including:
        a hollow member adapted to be disposed in an oral cavity of the subject when the medical instrument is attached to the subject, and
        a second housing defining a second airway communicating with the hollow member; and
    a joint connecting the nasal adapter and the bite block and forming a third airway communicating the first airway and the second airway,
    wherein the joint includes:
        a first connecting portion connected to the first housing,
        a second connecting portion connected to the second housing, and
        an intermediate portion arranged between the first connecting portion and the second connecting portion, and
    wherein a flexibility of the intermediate portion is greater than a flexibility of each of the first connecting portion and the second connecting portion; and wherein the joint has an opened side that faces a face of the subject when the medical instrument is attached to the subject.

2. The medical instrument according to claim 1, wherein the nasal adapter includes a support configured to support a sensor for detecting gas in the first airway.

3. The medical instrument according to claim 1, wherein one of the first connecting portion and the second connecting portion includes a portion having a larger dimension than the other of the first connecting portion and the second connecting portion in a direction corresponding to at least one of a left-right direction and a front-rear direction of a head of the subject when the medical instrument is attached to the subject.

4. The medical instrument according to claim 3, wherein the first connecting portion includes the portion having the larger dimension than the second connecting portion in the direction corresponding to at least one of the left-right direction and the front-rear direction of the head of the subject when the medical instrument is attached to the subject.

5. The medical instrument according to claim 1, wherein the intermediate portion includes a portion where a width of the third airway is narrowed in a direction corresponding to at least one of a left-right direction and a front-rear direction of a head of the subject when the medical instrument is attached to the subject.

6. The medical instrument according to claim 5, wherein the portion where the width of the third airway is narrowed has a bellows shape with a plurality of bent portions.

7. The medical instrument according to claim 1, wherein the joint is detachable with respect to at least one of the nasal adapter and the bite block.

8. The medical instrument according to claim 1, wherein a relative position between the nasal adapter and the bite block is variable in at least one of a plane including an up-down direction and a left-right direction of a head of the subject and a plane including a front-rear direction and the left-right direction of the head of the subject when the medical instrument is attached to the subject.

* * * * *